United States Patent
Quinn et al.

(10) Patent No.: US 10,052,096 B2
(45) Date of Patent: Aug. 21, 2018

(54) CHORDAL SIZER

(71) Applicant: On-X Life Technologies, Inc., Austin, TX (US)

(72) Inventors: Reed Quinn, Cumberland, ME (US); Kellen Moulton, Austin, TX (US); Ryan Medema, Pflugerville, TX (US)

(73) Assignee: On-X Life Technologies, Inc., Austin, TX (US)

( * ) Notice: Subject to any disclaimer, the term of this patent is extended or adjusted under 35 U.S.C. 154(b) by 548 days.

(21) Appl. No.: 14/551,844

(22) Filed: Nov. 24, 2014

(65) Prior Publication Data

US 2015/0148692 A1 May 28, 2015

Related U.S. Application Data

(60) Provisional application No. 61/907,904, filed on Nov. 22, 2013.

(51) Int. Cl.
| | |
|---|---|
| *A61B 5/02* | (2006.01) |
| *A61B 5/103* | (2006.01) |
| *A61B 5/117* | (2016.01) |
| *A61F 2/24* | (2006.01) |
| *A61B 17/04* | (2006.01) |
| *A61B 17/00* | (2006.01) |
| *A61B 90/00* | (2016.01) |

(52) U.S. Cl.
CPC .............. *A61B 17/0469* (2013.01); *A61B 2017/00243* (2013.01); *A61B 2017/0474* (2013.01); *A61B 2090/061* (2016.02); *A61F 2/2457* (2013.01)

(58) Field of Classification Search
CPC .......... A61F 2220/0025; A61F 2/2457; A61B 17/00234; A61B 17/0401; A61B 5/0205
USPC ................. 600/587, 481, 490; 623/2.1, 2.11
See application file for complete search history.

(56) References Cited

U.S. PATENT DOCUMENTS

| | | | | |
|---|---|---|---|---|
| 5,489,296 | A * | 2/1996 | Love .................... | A61F 2/2496 600/587 |
| 6,231,601 | B1 * | 5/2001 | Myers .................. | A61F 2/2466 294/24 |

(Continued)

OTHER PUBLICATIONS

Edwards Lifescience, "ThruPort System," Product Catalog, AR09399, rev date Apr. 2013, 30 pages.

(Continued)

*Primary Examiner* — May Abouelela
(74) *Attorney, Agent, or Firm* — Trop, Pruner & Hu, P.C.

(57) ABSTRACT

An embodiment includes a cardiovascular surgical apparatus comprising: a sleeve including a distal sleeve end, a proximal sleeve end, and a sleeve long axis extending from the distal sleeve end to the proximal sleeve end; a post including a distal post end and a proximal post end; a first projection member, coupled to the distal sleeve end, including a first projection member main body and a first projection member retention body; a second projection member coupled to the proximal sleeve end; wherein (a) the post telescopes distally from within the sleeve and away from the distal sleeve end; (b) at least one of the first and second projection members rotates at least 45 degrees with respect to another of the first and second projection members; and (c) the first projection member retention body includes a long axis generally parallel to the sleeve long axis. Other embodiments are described herein.

19 Claims, 7 Drawing Sheets

(56) References Cited

U.S. PATENT DOCUMENTS

| | | | |
|---|---|---|---|
| 6,598,307 B2* | 7/2003 | Love | A61B 5/1076 33/512 |
| 7,431,692 B2* | 10/2008 | Zollinger | A61B 17/0401 600/37 |
| 8,449,625 B2* | 5/2013 | Campbell | A61B 5/1076 600/587 |
| 9,480,562 B2* | 11/2016 | Gillinov | A61F 2/2457 |
| 2003/0105519 A1* | 6/2003 | Fasol | A61F 2/2457 623/2.1 |
| 2007/0255396 A1* | 11/2007 | Douk | A61B 17/083 623/2.1 |
| 2009/0088837 A1* | 4/2009 | Gillinov | A61B 5/1072 623/2.1 |
| 2009/0281619 A1* | 11/2009 | Le | A61M 25/01 623/2.11 |
| 2010/0161041 A1* | 6/2010 | Maisano | A61B 17/0401 623/2.1 |
| 2010/0249919 A1* | 9/2010 | Gillinov | A61F 2/2427 623/2.11 |
| 2010/0312332 A1* | 12/2010 | Forster | A61F 2/2418 623/2.1 |
| 2012/0184971 A1* | 7/2012 | Zentgraf | A61B 1/018 606/144 |
| 2013/0013056 A1* | 1/2013 | Chawla | A61F 2/2457 623/2.11 |
| 2013/0178930 A1* | 7/2013 | Straubinger | A61F 2/2436 623/2.1 |
| 2013/0231735 A1* | 9/2013 | Deem | A61F 2/243 623/2.11 |
| 2013/0289717 A1* | 10/2013 | Solem | A61M 1/1081 623/2.11 |
| 2014/0114403 A1* | 4/2014 | Dale | A61B 17/0644 623/2.11 |
| 2014/0135909 A1* | 5/2014 | Carr | A61F 2/2436 623/2.11 |
| 2014/0142689 A1* | 5/2014 | De Canniere | A61F 2/2457 623/2.11 |
| 2014/0155990 A1* | 6/2014 | Nyuli | A61F 2/2418 623/2.11 |

OTHER PUBLICATIONS

Gillinov, Marc, et al., "Pre-Measured Artificial Chordae for Mitral Valve Repair," http://ats.ctsnetjournals.org/cgi/content/full/84/6/2127, Department of Thoracic and Cardiovascular Surgery, The Cleveland Clinic, Cleveland, Ohio, Ann Thorac Surg 2007;84:2127-2129.

Geister Medizintechnik GmbH, "ValveGate PRO," Product Brochure, www.geister.com, Tuttlingen, Germany, 2011, 28 pages.

* cited by examiner

CHORDAL SIZER

PRIORITY CLAIM

This application claims priority to U.S. Provisional Patent Application No. 61/907,904 filed on Nov. 22, 2013 and entitled "Chordal Sizer", the content of which is hereby incorporated by reference.

BACKGROUND

As addressed in U.S. patent application Ser. No. 12/750, 800, heart valve replacement is a well-known procedure in which an artificial heart valve prosthesis is implanted in place of a diseased or malfunctioning heart valve. Heart valve prostheses may be mechanical or bioprosthetic. Use of mechanical valves typically requires extensive anticoagulation therapy. The need for anticoagulation therapy can be avoided in general by the use of artificial biological heart valves, such as bovine xenografts. Nevertheless, dystrophic calcification with subsequent degeneration is a cause of failure of such bioprostheses in the long term. When mitral or tricuspid valve replacement is performed, the chordae tendineae are cut, thus leaving the geometry and function of the ventricle impaired and in need of reconstruction.

As an alternative to conventional heart valve replacement operations, diseased and malfunctioning chordae can be repaired by surgically replacing diseased heart chordae with artificial chordae. One known way of replacing a malfunctioning chordae uses a simple suture with a needle on each end of the suture. The suture is stitched through the papillary muscle and secured thereto with a knot. The two ends of the suture are then similarly stitched through the free ends of the valve leaflets. The valve will not function properly if the length of the artificial chordae between the papillary muscle and valve leaflet is overly long or overly short. Replacement chords are discussed more specifically in, for example, U.S. patent application Ser. Nos. 12/750,800 and 12/238,322.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Reference will now be made to the drawings wherein like structures may be provided with like suffix reference designations. In order to show the structures of various embodiments more clearly, the drawings included herein are diagrammatic representations of devices and may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

An embodiment helps a healthcare provider better determine the correct chord size for valve repair related chord replacement. An embodiment provides features that allow the surgeon to more easily tie the correct size of loop for chord replacement. An embodiment includes a chordal sizer that is a single-use medical device that assists the surgeon in determining the correct size of a chordae tendineae prosthetic loop (or functional equivalent thereof) to implant in mitral valve repair surgery. Once the loop size is determined, the chordal sizer can also be used as an instrument to quickly tie loops of the correct size, or it indicates to the surgeon which size of pre-configured loops prosthesis to select.

Figure 1:
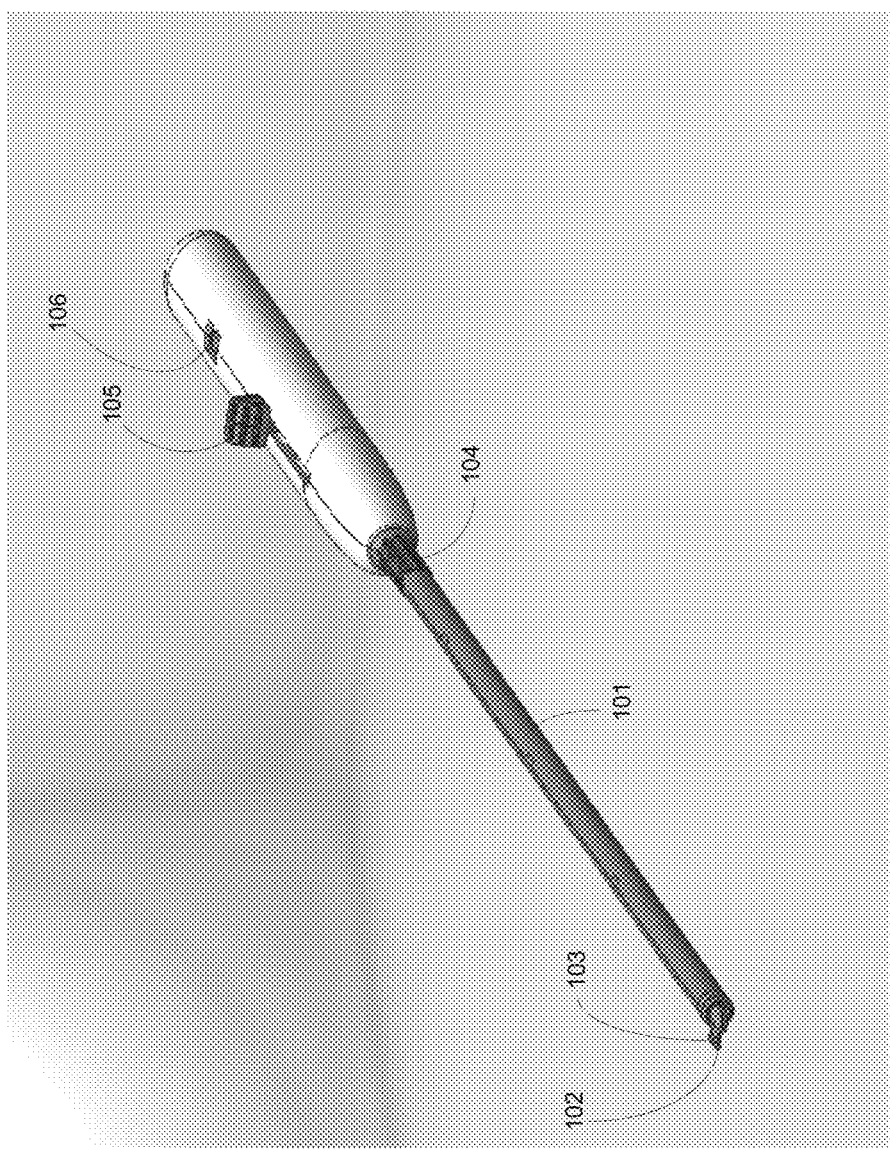
FIG. 1 includes a perspective view of an embodiment of the invention.
Figure 2:
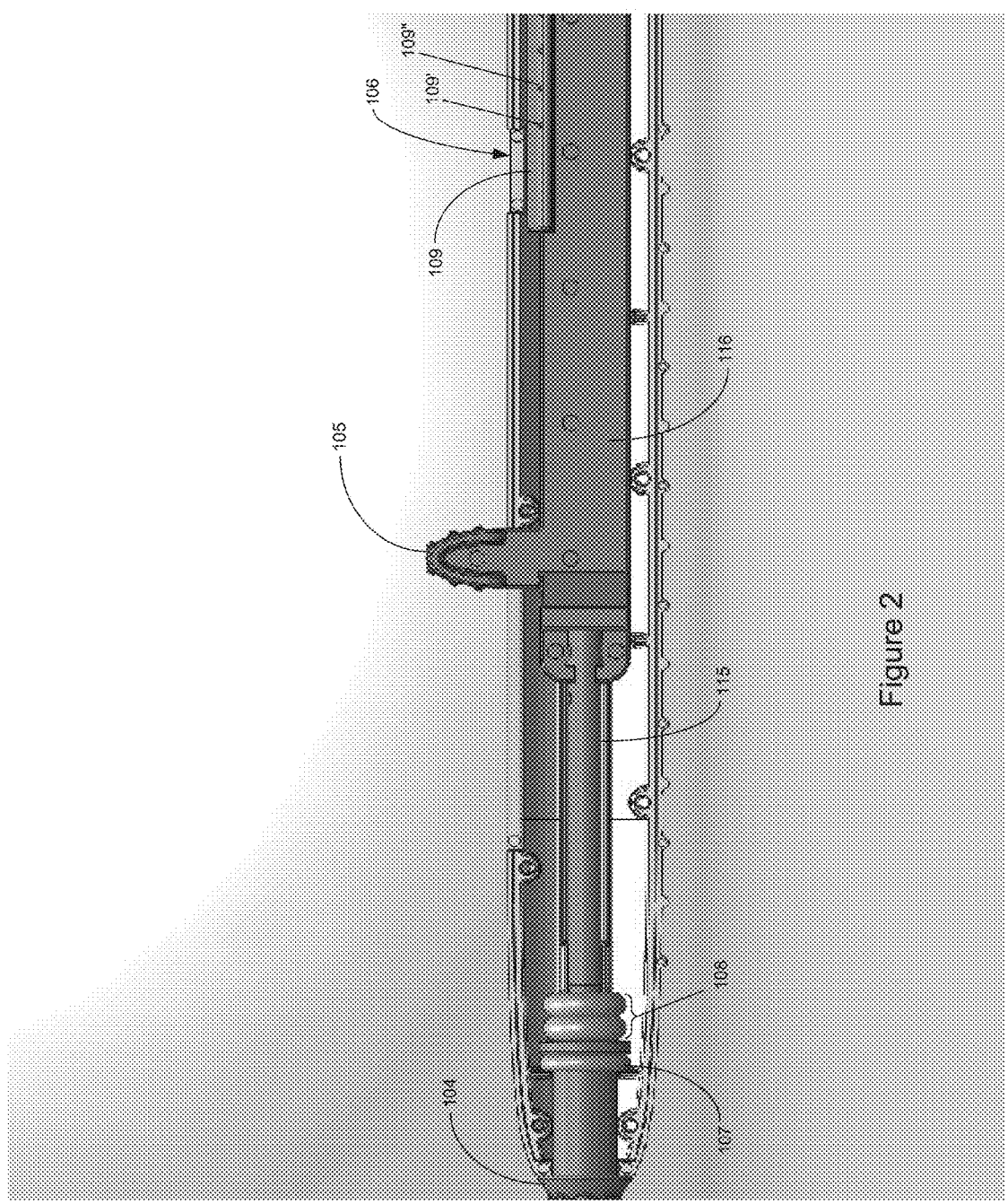
FIG. 2 includes a side cross-sectional view of an embodiment of the invention.
Figure 3:
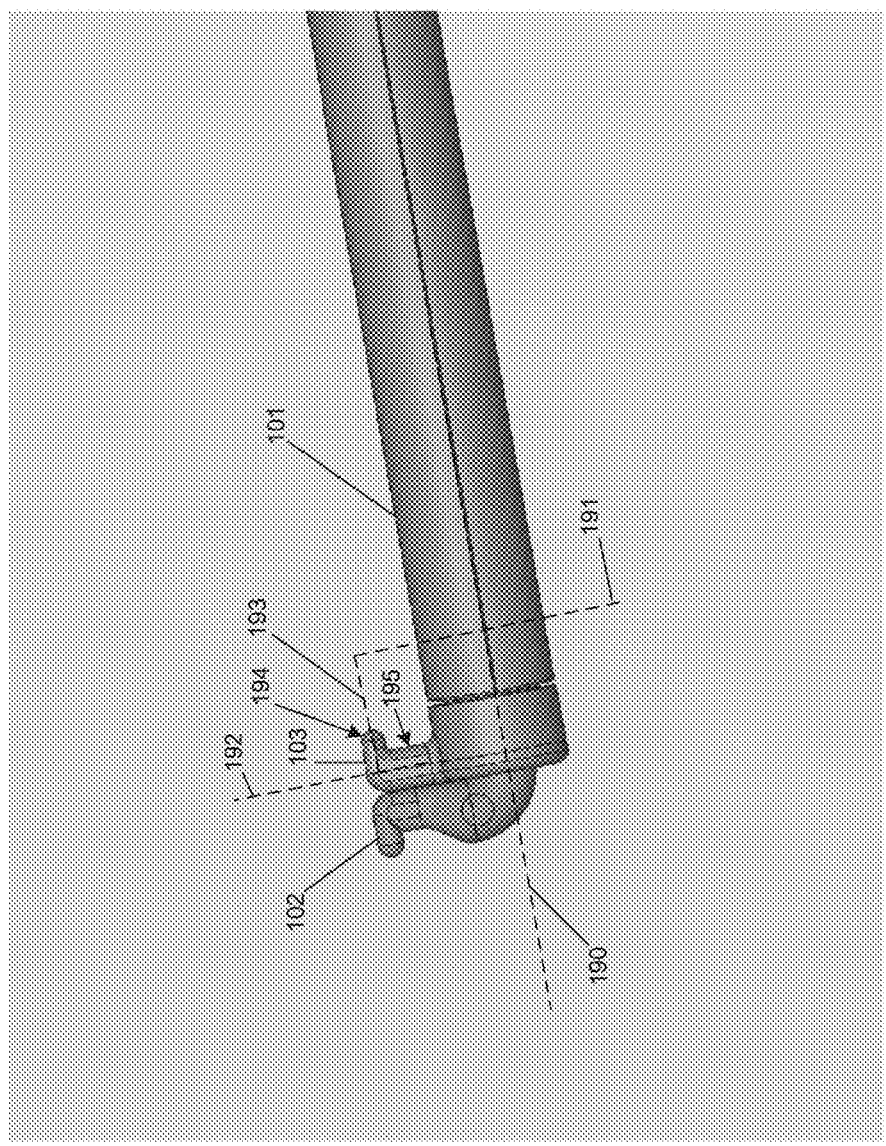
FIG. 3 includes a perspective view of "hooks" in an embodiment of the invention.
Figure 4:
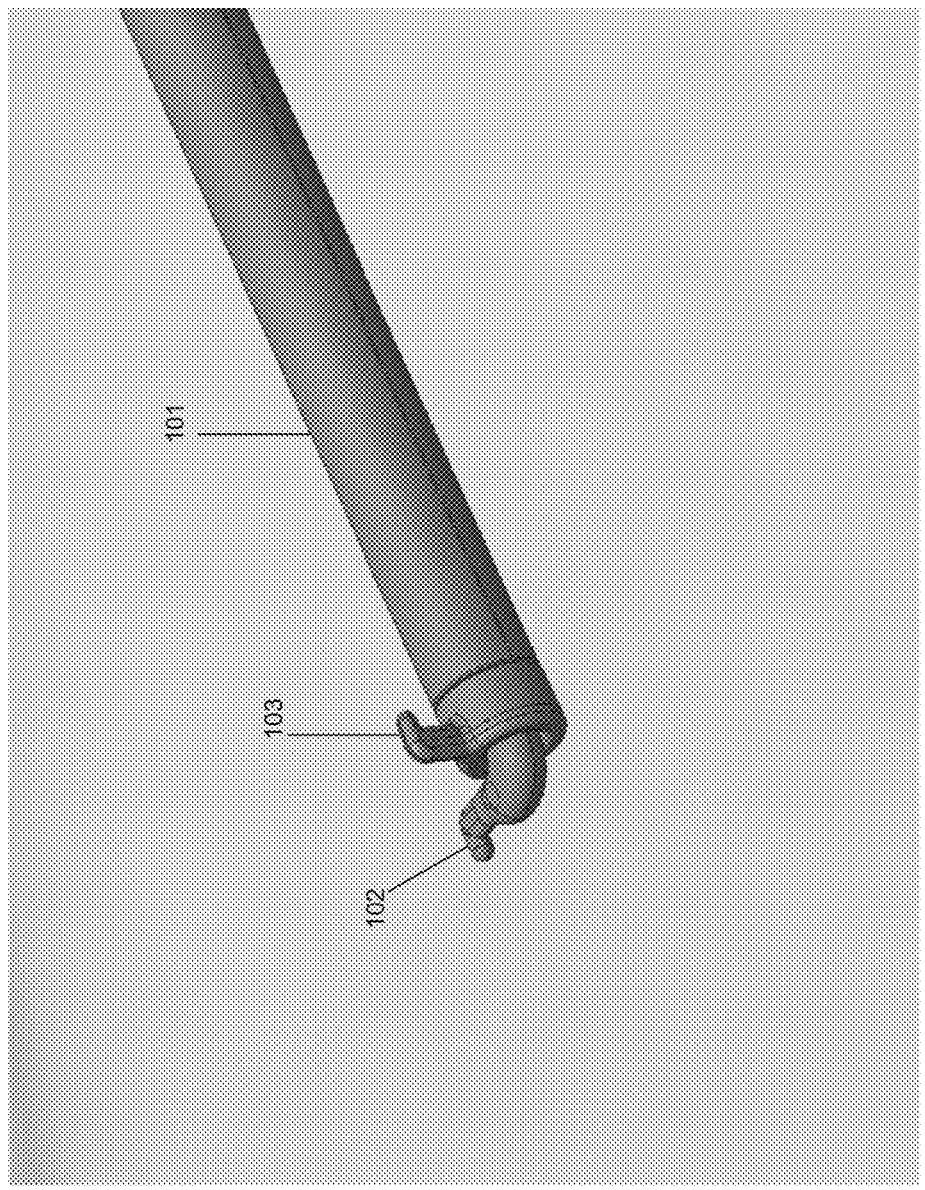
FIG. 4 includes a perspective view of rotated hooks in an embodiment of the invention.

FIG. 1 includes a perspective view of an embodiment of the invention. System 100 includes projections 102, 103 (see also FIG. 3) at, in an undeployed state, a distal end portion of barrel or sleeve 101. Barrel 101 may be rotated by rotating dial or handling portion 104, thereby not only rotating barrel 101 but also rotating projection 103. As a result, projection 102 may be rotated between 0 and 360 degrees from projection 103. FIG. 4 shows a rotation of about 90 degrees whereas FIG. 3 shows a rotation of about 0 degrees. In an embodiment rotating dial 104 may only rotate one of projections 102, 103 without necessarily rotating barrel 101. An embodiment may rotate projection 102 and not projection 103 with or without rotating barrel 101. Projection 102 may deploy from barrel 101 (via deployment of shaft, rod, or post 115 in FIG. 2) and away from projection 103 by advancing lever 105 (and shaft 115) distally and projection 102 may retreat towards barrel 101 and towards projection 103 by withdrawing level 105 (and shaft 115) proximally. In an embodiment barrel 101 does not rotate but instead shaft 115 rotates to thereby rotate projection 102 and/or projection 103. In an embodiment both projections 102, 103 may rotate.

In an embodiment, the amount of deployment of projection 102 from projection 103 is indicated by viewing through window 106 at scale 109, which includes indicators (e.g., changes in color, raised notches or projections) 109', 109" (see FIG. 2) that translate into a length of desired artificial chord. For example, scale 109 is printed on a label and coupled to shuttle 105 via coupling member 116. Scale 109 may have color-coded regions that correspond with the label colors for pre-measured loops products. Thus a measurement in the "blue" area of scale 109 may indicate the need to use pre-sized chord A but a measurement in the yellow area of scale 109 may indicate the need to use pre-sized chord B. Pre-sized chords A and B may be included in a package delivered to the hospital from which the doctor may select the proper length of chord after measuring the patient's anatomy. Not all embodiments include a scale.

An embodiment is made with injection molded plastics. Silicone O-rings provide friction internal to the device. Specifically, O-rings 107, 108 (FIG. 2) may help provide some element of resistance towards deployment of projection 102 from projection 103 and/or rotation of projection 102 with respect to projection 103. In an embodiment one O-ring 107 fits around the back of barrel 101. This O-ring provides compression to hold the barrel flush against the housing pieces. It allows the barrel to rotate (i.e., to rotate the leaflet hook 103 in relation to the papillary pointer 102) when enough force is provided to overcome the friction. The other two O-rings 108 are adjacent each other and fit around the shaft 115. These two O-rings are held in place by features in the housing. The shaft 115 can be advanced by sliding shuttle 105. The two O-rings 108 on the shaft 115 provide friction to prevent the shaft 115 from moving unintentionally. O-rings 107, 108 may reside in grooves (not shown) in shaft 115 so the O-rings are unstressed during shipping and storage and will not relax.

Figure 5:
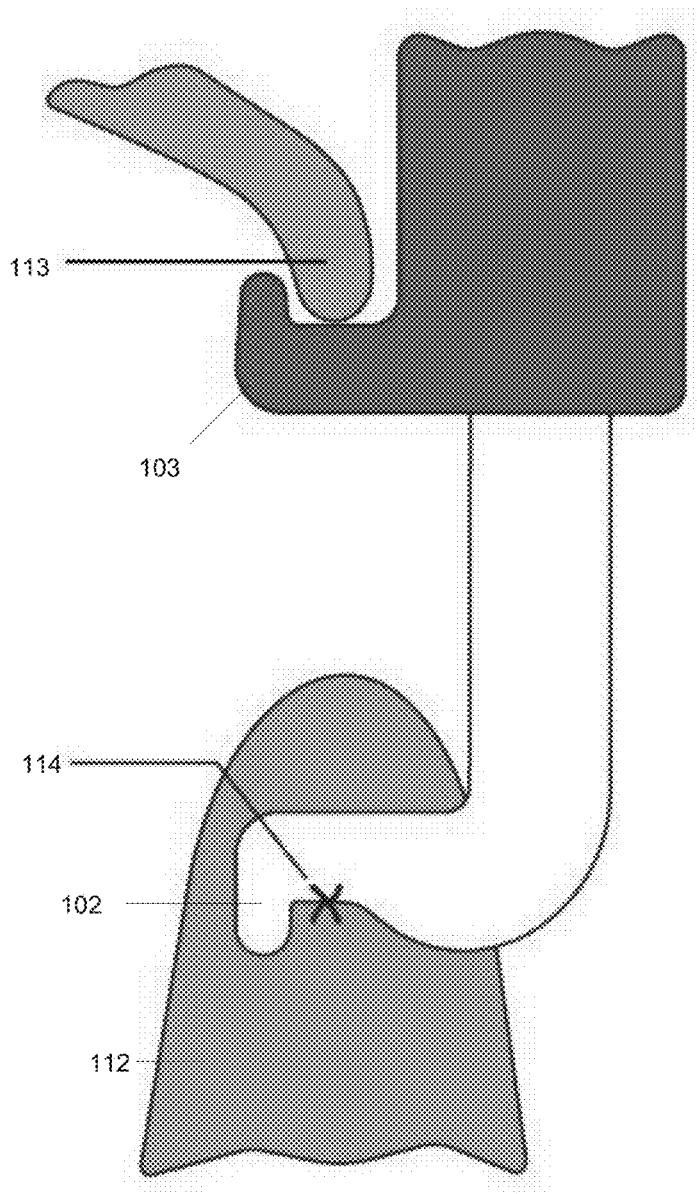
FIG. 5 includes a perspective view of hooks coupled to cardiac tissue in an embodiment of the invention.

As seen in FIG. 5, in an embodiment projection 103 may be considered a form of hook or cradle with which to retain or support leaflet 113. Projection 103 hooks/stabilizes mitral valve leaflet 113, allowing the surgeon to manipulate leaflet 113 into a desired position. Projection 102 serves as a "papillary pointer" that extends and points toward the papillary muscle. Location 114 indicates the planned site of desired papillary muscle attachment. In an embodiment projections 102, 103 are orthogonal to one another (or at least not in-line with each other) when leaflet 113 is hooked or restrained (see FIG. 4). This orientation allows the surgeon to more clearly see where the papillary pointer is pointing considering projection 103 will now no longer block a view of projection 102 and the papillary muscle. The papillary pointer 102 does not hook onto any part of the heart in an embodiment. A portion (see element 114 of FIG. 5) of projection 102 simply points to the location on the papillary muscle where the surgeon would like to implant the prosthetic chords to determine the proper length of the chord(s).

In an embodiment, the health care provider (e.g., surgeon) can tie suture loops directly around the papillary pointer 102 and the leaflet hook 103. As used herein, "hook" is not mean to include a piecing object but more to include a retention member used to retain, support, or stabilize tissue, such as a heart valve leaflet.

Figure 6:
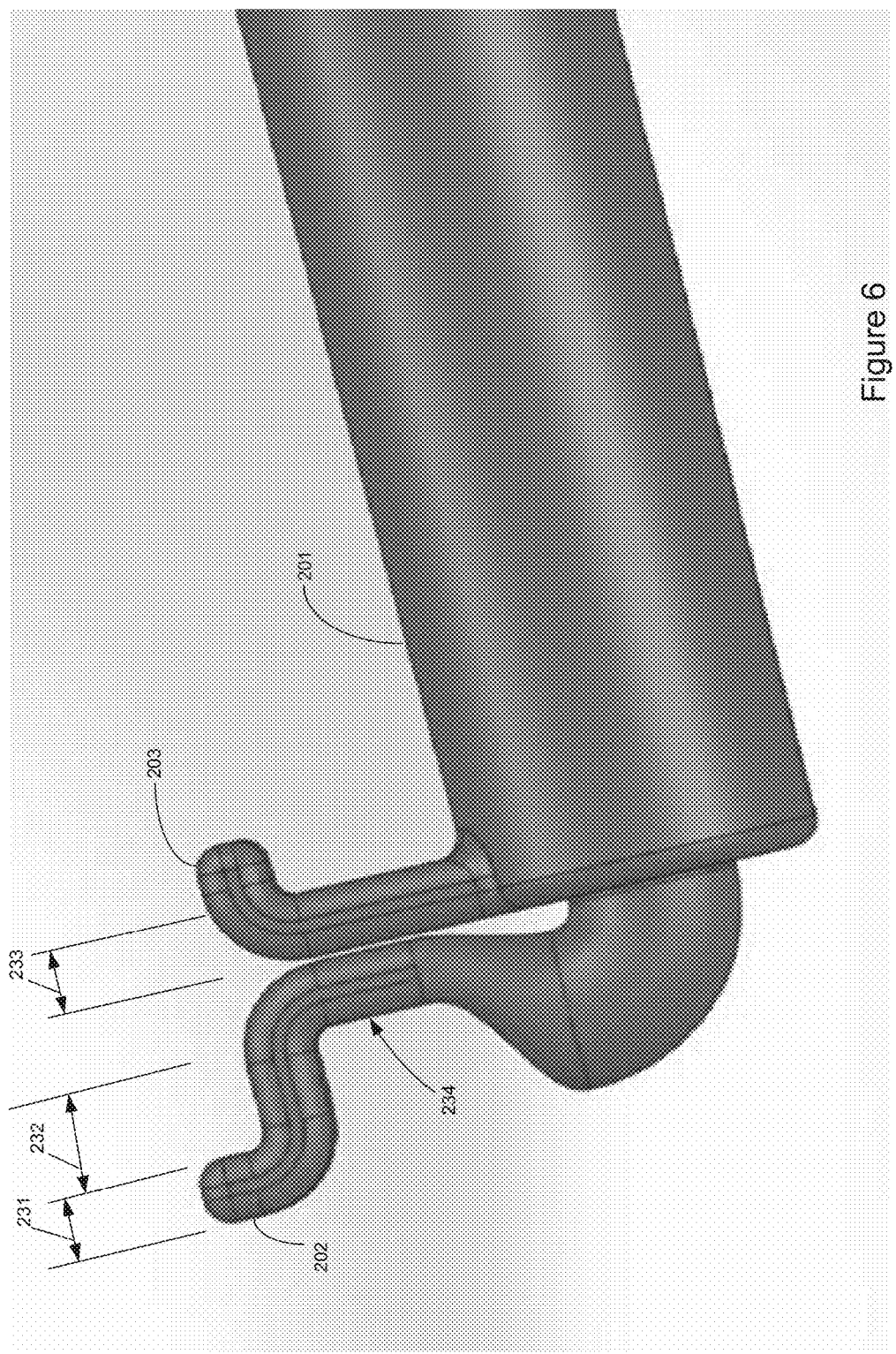
FIG. 6 includes a perspective view of offset hooks in an embodiment of the invention.

FIG. 6 includes an embodiment that accounts for potential measurement errors. For example, because projections 202, 203 are each a few millimeters wide (see distances 231 and 233), a loop tied around the projections may be larger than the distance between the portions of the projections that indicate exactly where the physician desires loop placement. To correct for this, the papillary pointer feature 202 is offset several millimeters (distance 232) from where the suture is tied at location 234. Regarding this offset, this offset may be to varying degrees. For example, the offset (shown in FIG. 6 as distance 232) may directly equal the sum of the widths or areas of thickness (both shown in FIG. 6 as distances 231, 233), may be slightly less or more than this sum, and the like.

Figure 7:
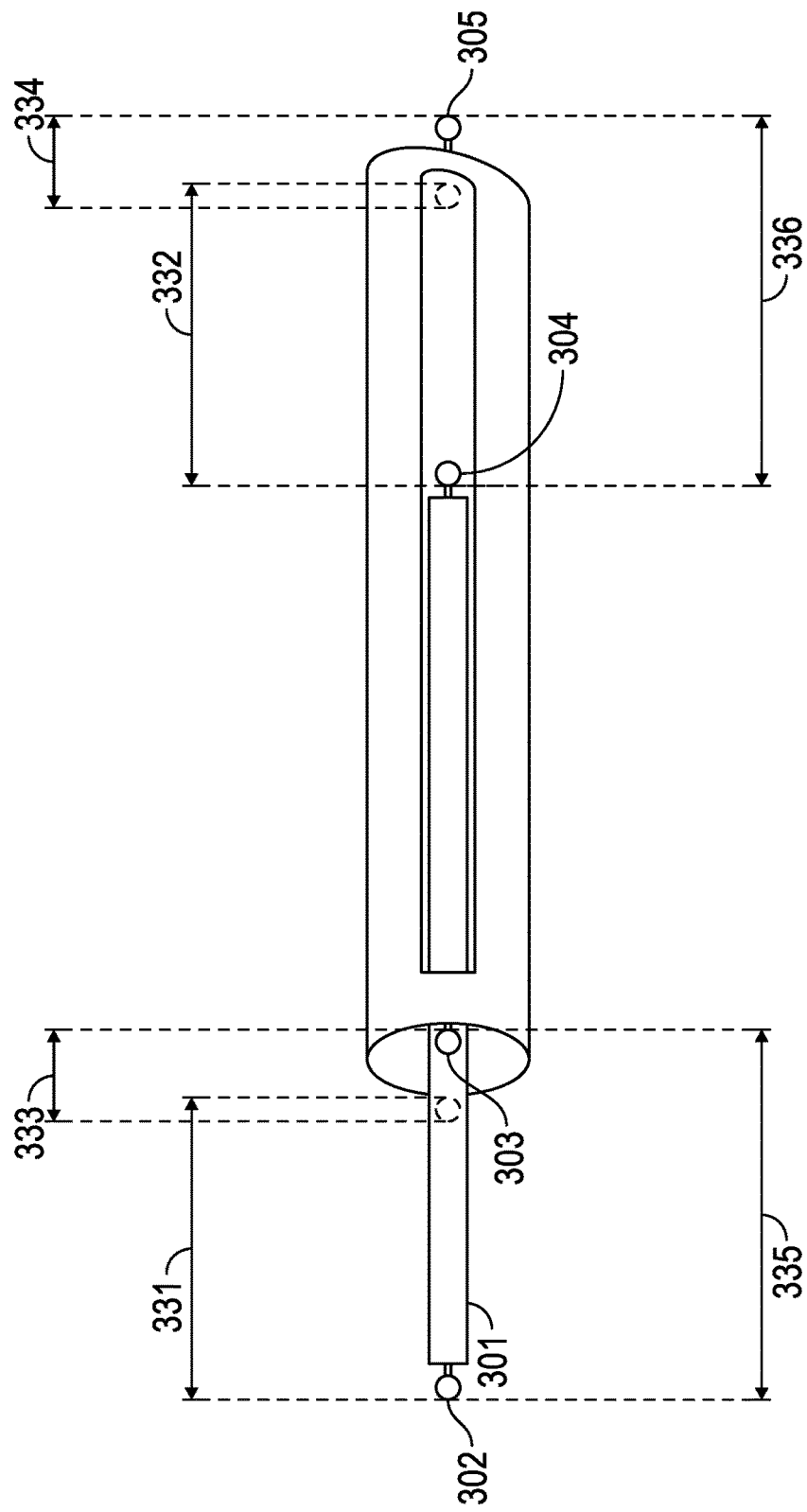
FIG. 7 includes a side view of an embodiment of the invention.

In an embodiment the measuring features 102, 103 at the distal end portion of system 100 may be separated from the loop tying features. Separate loop tying features could possibly be placed further back on the device. For example, see FIG. 7. This embodiment shows how the doctor could use posts 302, 303 to measure the proposed chord length and then use posts 304, 305 for tying the proper length of chord. Posts 304, 305 could be much larger than posts 302, 303 since they are not placed in the patient (unlike posts 302, 303) and these larger posts may facilitate knot tying and the like. The distance 335 between posts 302, 303 is equal to the distance 336 between posts 304, 305. This equality of distances is seen in both the deployed and undeployed positions (e.g., distance 331 equals distance 332 in an undeployed state and distance 335 equals distance 336 in a deployed state).

An embodiment includes a method for determining proper chord length. The method may use an embodiment such as the embodiment of FIG. 1, which assists the surgeon in determining the proper length of chordal replacement prostheses needed to repair the mitral valve. It may be used to help the surgeon select a preconfigured prosthesis, or to easily configure the correct size using straight suture material, during mitral valve repair.

In the method the physician first uses leaflet hook 103 to support the edge of the leaflet 113 in the desired position. The physician then uses thumb-slide 105 to extend the papillary hook 102 to the planned site 114 of attachment to the papillary muscle 112 as shown in FIG. 5. The slide 105 may lock automatically when the physician no longer pushes or pulls upon it. The leaflet hook 103 may be rotated to any desired angle relative to the papillary hook 102 to improve visibility while the papillary pointer 102 points to the desired attachment site 114. The physician rotates the leaflet hook 103 by using the grips 104 at the base of the barrel 101. The colors/projections 109, 109" of scale 109 match the label colors for corresponding pre-measured loops prostheses with a variety of sizes being made available in a kit. The scale indicator (e.g., a number or color or projection) indicates the size of chordal loops produced by tying suture around the two hooks 102, 103. The physician rotates the barrel 101 so that the leaflet hook 103 is again aligned with the papillary hook 102 (after having been rotated away from papillary hook during measuring) prior to tying loops around projections 102, 103. Thus, the physician can rotate hooks 102, 103 with regard to one another to achieve better site visibility without affecting the measured length. After tying loops around projections 102, 103, the physician pulls the papillary hook 102 back to remove tied loop or loops from the hooks 102, 103. Once the artificial chordae tendineae are in place, a saline test may be performed to verify that the chordal loop size is correct and that the valve is competent.

One or more embodiments provide several advantages such as, without limitation: (1) offset of the papillary pointer 202, 203 and the feature that suture is tied around (see, e.g., FIG. 6), (2) rotating leaflet hook (e.g., FIG. 4), (3) color-coded scale (e.g., element 109), (4) using O-rings 108, 109 for friction to stabilize projection deployment and placement, and (5) tying the sutures using posts that are proximal to the papillary pointing element (e.g., FIG. 7). Various embodiments include only a selected one of (1)-(5) while other embodiments include some or all of (1)-(5). Thus, embodiments recognize a previously underappreciated problem regarding the visualization of papillary muscle while retaining a leaflet and provides a solution that provides better visualization while retaining accurate chord length measurement.

While scale 109 was indicated as a good way to measure the length of desired cords based on distances between projections 102, 103, in an embodiment a physician may use an image (e.g., echocardiogram) to determine a length and then "dial" in that length using scale 109. Afterwards the loops can be quickly tied using projections 102, 103. In some embodiments, if the physician is using the system 100 to both measure and tie loops, the scale 109 may be unnecessary. However, using scale 109 in such a situation would allow the physician to quickly reset the hooks 102, 103 if for whatever reason the hooks were moved from their proper separation from one another.

In an embodiment the hooks 102, 103 rotate in 90 degree intervals whereby one of the hooks "clicks" into place at 90 degree intervals based on notches and spring member systems used to retain a member within a notch until the member is forcibly removed from the notch in order to rotate hooks 102, 103 about each other.

Even if there is no permissible rotation of projections 102, 103 with respect to each other, in an embodiment the two projections 102, 103 may be permanently offset with each other (i.e., a line connect the two points is not collinear or parallel to a long axis of the device). In such a situation a third projection may be included such that first projection is located where element 102 is in FIG. 3, a second projection is located where element 103 is located in FIG. 3, and simultaneously a third projection is located where element 103 is located in FIG. 4. In other words, the device may be simplified by removing the rotation element and providing "two static versions" of element 103, one to measure (i.e., the rotated version) and another for tying. In another embodiment, a third projection may be included such that a first projection is located where element 103 is in FIG. 3, a second projection is located where element 102 is located in FIG. 3, and simultaneously a third projection is located where element 102 is located in FIG. 4. In other words, the device may be simplified by removing the rotation element and providing "two static versions" of element 102, one to measure (i.e., the rotated version) and another for tying. The embodiment may provide the two static versions of element 102 are co-planar with each other and one of the two static versions of element 102 and element 103 are co-planar with each other. These two planes may be orthogonal to each other in an embodiment but not necessarily so in other embodiments.

An embodiment is used in chordae tendineae repair. However, other embodiments may be used to make measurements in the heart for other procedures. For example, Ventricular Septal Defect (VSD) patches need to be the correct size, and this instrument may be used for such a purpose. Also, tricuspid valve repair and the like are also options.

An embodiment includes a cardiovascular surgical apparatus comprising: a sleeve including a distal sleeve end, a proximal sleeve end, and a sleeve long axis (e.g., axis 190 of FIG. 3, which is orthogonal to sleeve short axis 191) extending from the distal sleeve end to the proximal sleeve end.

The sleeve may be a conduit but is not so limited and may include, for example only, a member with a channel included therein. For example, a gutter for a house or a bowling alley lane may include a "sleeve" which could function as a channel for rod 115. A "long axis" as used herein is the longest of the main axes for an object and is an imaginary line passing longitudinally through the center of a body.

The body further includes a post (e.g., rod) including a distal post end and a proximal post end; a first projection member, coupled to the distal sleeve end, including a first projection member main body (e.g., element 195) and a first projection member retention body (e.g., element 194); and a second projection member coupled to the proximal sleeve end.

In the embodiment (a) the first and second projection members (e.g., projections 102, 103) both project outwards and away from the sleeve long axis; (b) the post telescopes distally from within the sleeve and away from the distal sleeve end; (c) at least one of the first and second projection members rotates at least 45 degrees about the sleeve long axis and with respect to another of the first and second projection members; and (d) the first projection member retention body includes a long axis (e.g., axis 193) generally parallel to the sleeve long axis. In an embodiment the first projection member main body includes a long axis (e.g., axis 192) generally orthogonal to the sleeve long axis (e.g., axis 190).

In an embodiment at least one of the first and second projection members rotates at least 15, 25, 35, 45, 55, 65, 75, 85, 90, 100, 110, 120, 130, 140, 150, 160, 170, 180 degrees or more about the sleeve long axis and with respect to another of the first and second projection members.

While projections 103, 103 include "L" shaped members other projections in other embodiments may not necessarily include "L" shaped members but may instead include a sphere or ball affixed to a post that projects away from axis 190 (orthogonally or otherwise). Projection 102, 103 include portions that project away from axis 190. They may do so at 90 degree angles (see FIG. 3) or otherwise such as 30, 45, 60, 110, 130, 145, 160, 180 degrees and the like. In an embodiment projection 103 may include an "L" member while projection 102 is merely a pointer with which to point at muscle tissue but not necessarily configured to retain or support tissue.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A cardiovascular surgical apparatus comprising:
a sleeve including a distal sleeve end, a proximal sleeve end, and a sleeve long axis extending from the distal sleeve end to the proximal sleeve end;
a post including a distal post end and a proximal post end;
a first hook coupled to the distal sleeve end;
a second hook coupled to the distal post end; and
a rotator selected from the group consisting of a dial and a handle, the rotator being configured to rotate one of the first and second hooks;
wherein: the post telescopes distally from within the sleeve and away from the distal sleeve end;
the first hook rotates between 45 and 360 degrees (i) about the sleeve long axis and with respect to the second hook, and (ii) in response to actuation of the rotator;
the first hook includes a projection member that (i) projects outwards and away from the sleeve long axis, and (ii) points proximally toward the proximal sleeve end; and
the second hook includes a projection member that (i) projects outwards and away from the sleeve long axis, and (ii) points distally away from the proximal sleeve end.

2. The apparatus of claim 1 wherein the first hook connects directly and fixedly to the distal sleeve end.

3. The apparatus of claim 1 wherein the sleeve rotates between 45 and 360 degrees with respect to the post.

4. The apparatus of claim 1 wherein the first hook rotates between 45 and 360 degrees about the sleeve long axis in response to the sleeve rotating between 45 and 360 degrees with respect to the post.

5. The apparatus of claim 1 including a scale having a measurement that changes in response to the post telescoping distally from within the sleeve and the measurement corresponds to a distance between the first and second hooks.

6. The apparatus of claim 1, wherein the second hook is distal to the first hook and the first hook is between the second hook and the proximal sleeve end.

7. A cardiovascular surgical apparatus comprising:
a sleeve including a distal sleeve end, a proximal sleeve end, and a sleeve long axis extending from the distal sleeve end to the proximal sleeve end;
a post including a distal post end and a proximal post end;
a first hook coupled to the distal sleeve end;
a second hook coupled to the distal post end; and
a rotator selected from the group consisting of a dial and a handle, the rotator being configured to rotate one of the first and second hooks;
wherein: the post telescopes distally from within the sleeve and away from the distal sleeve end;
the second hook rotates between 45 and 360 degrees (i) with respect to the first hook, and (ii) in response to actuation of the rotator;
the first hook includes a projection member that (i) projects outwards and away from the sleeve long axis, and (ii) points proximally toward the proximal sleeve end; and
the second hook includes a projection member that (i) protects outwards and away from the sleeve long axis, and (ii) points distally away from the proximal sleeve end.

8. The apparatus of claim 7 wherein the first hook connects directly and fixedly to the distal sleeve end.

9. The apparatus of claim 7 wherein the sleeve rotates between 45 and 360 degrees with respect to the post.

10. The apparatus of claim 7 wherein the second hook rotates between 45 and 360 degrees about the sleeve long axis in response to the sleeve rotating between 45 and 360 degrees with respect to the post.

11. The apparatus of claim 7 including a scale having a measurement that changes in response to the post telescoping distally from within the sleeve and the measurement corresponds to a distance between the first and second hooks.

12. The apparatus of claim 7, wherein the second hook is distal to the first hook and the first hook is between the second hook and the proximal sleeve end.

13. A cardiovascular surgical apparatus comprising:
a sleeve including a distal sleeve end, a proximal sleeve end, and a sleeve long axis extending from the distal sleeve end to the proximal sleeve end;
a post including a distal post end and a proximal post end;
a first hook coupled to the distal sleeve end;
a second hook coupled to the distal post end; and
a rotator selected from the group consisting of a dial and a handle, the rotator configured to rotate one of the first and second hooks with respect to another of the first and second hooks;
wherein:
the post telescopes distally from within the sleeve and away from the distal sleeve end;
at least one of the first and second hooks rotates between 45 and 360 degrees about the sleeve long axis and another of the first and second hooks in response to actuation of the rotator;
the first hook includes a projection member that (i) projects outwards and away from the sleeve long axis, and (ii) points proximally toward the proximal sleeve end; and
the second hook includes a projection member that (i) projects outwards and away from the sleeve long axis, and (ii) points distally away from the proximal sleeve end.

14. The apparatus of claim 13 wherein the first hook connects directly and fixedly to the distal sleeve end.

15. The apparatus of claim 13 wherein the sleeve rotates between 45 and 360 degrees with respect to the post.

16. The apparatus of claim 13 wherein the at least one of the first and second hooks rotates between 45 and 360 degrees about the sleeve long axis in response to the sleeve rotating between 45 and 360 degrees with respect to the post.

17. The apparatus of claim 13 wherein the at least one of the first and second hooks rotates between 45 and 360 degrees about the sleeve long axis in response to the post rotating between 45 and 360 degrees with respect to the sleeve.

18. The apparatus of claim 13 including a scale having a measurement that changes in response to the post telescoping distally from within the sleeve and the measurement corresponds to a distance between the first and second hooks.

19. The apparatus of claim 13, wherein the second hook is distal to the first hook and the first hook is between the second hook and the proximal sleeve end.

\* \* \* \* \*

UNITED STATES PATENT AND TRADEMARK OFFICE
CERTIFICATE OF CORRECTION

PATENT NO. : 10,052,096 B2  
APPLICATION NO. : 14/551844  
DATED : August 21, 2018  
INVENTOR(S) : Reed Quinn et al.

Page 1 of 1

It is certified that error appears in the above-identified patent and that said Letters Patent is hereby corrected as shown below:

Column 7, Claim 7, Line 33, "protects outwards and away from the sleeve long axis" should be --projects outwards and away from the sleeve long axis--.

Signed and Sealed this  
Ninth Day of October, 2018

Andrei Iancu  
*Director of the United States Patent and Trademark Office*